(12) United States Patent
Fares et al.

(10) Patent No.: US 10,314,774 B2
(45) Date of Patent: Jun. 11, 2019

(54) CLEAR WET SPRAYS AND GELS

(75) Inventors: Hani M. Fares, Somerset, NJ (US);
Donald I. Prettypaul, Englewood, NJ (US); Diane M. Kennedy, Bayonne, NJ (US)

(73) Assignee: ISP Investment LLC, Wilmington, DE (US)

( * ) Notice: Subject to any disclaimer, the term of this patent is extended or adjusted under 35 U.S.C. 154(b) by 0 days.

(21) Appl. No.: 14/110,955

(22) PCT Filed: Apr. 27, 2012

(86) PCT No.: PCT/US2012/035501
§ 371 (c)(1),
(2), (4) Date: Oct. 10, 2013

(87) PCT Pub. No.: WO2012/149355
PCT Pub. Date: Nov. 1, 2012

(65) Prior Publication Data
US 2014/0030198 A1    Jan. 30, 2014

Related U.S. Application Data

(60) Provisional application No. 61/488,237, filed on May 20, 2011, provisional application No. 61/479,578, filed on Apr. 27, 2011.

(51) Int. Cl.
| | | |
|---|---|---|
| *A61K 8/49* | (2006.01) | |
| *A61Q 17/04* | (2006.01) | |
| *A61K 8/368* | (2006.01) | |
| *A61K 8/34* | (2006.01) | |
| *A61K 8/35* | (2006.01) | |
| *A61K 8/37* | (2006.01) | |
| *A61K 8/40* | (2006.01) | |
| *A61K 8/36* | (2006.01) | |
| *A61Q 19/00* | (2006.01) | |

(52) U.S. Cl.
CPC ............... *A61K 8/368* (2013.01); *A61K 8/34* (2013.01); *A61K 8/35* (2013.01); *A61K 8/36* (2013.01); *A61K 8/37* (2013.01); *A61K 8/40* (2013.01); *A61Q 17/04* (2013.01); *A61Q 19/00* (2013.01); *A61K 2800/31* (2013.01)

(58) Field of Classification Search
CPC ..................................................... A61Q 19/00
See application file for complete search history.

(56) References Cited

U.S. PATENT DOCUMENTS

| | | | |
|---|---|---|---|
| 4,193,989 A | * | 3/1980 | Teng et al. .......... 424/60 |
| 5,444,096 A | | 8/1995 | Mccrea et al. |
| 6,165,450 A | | 12/2000 | Chaudhuri et al. |
| 2005/0112188 A1 | | 5/2005 | Eliaz et al. |
| 2009/0324659 A1 | | 12/2009 | Polonka et al. |
| 2010/0221195 A1 | | 9/2010 | Tamarkin |

OTHER PUBLICATIONS

International Search Report, PCT/US2012/035501, published on Nov. 1, 2012.

* cited by examiner

*Primary Examiner* — Hasan S Ahmed
(74) *Attorney, Agent, or Firm* — William J. Davis; Shorong Chen; Nathalie Tietcheu

(57) ABSTRACT

Sun-care products are described that protect from UV radiation and do not turn white when applied to wet skin. The sun-care product may comprise (A) a cosmetically-acceptable, substantially non-aqueous vehicle, and (B) a UV active, wherein said non-aqueous vehicle comprises alcohol in an amount of 50% (w/w) or less based on the weight of the sun-care product and an ester wherein said non-aqueous vehicle comprises at least 10%>by weight esters based on the total weight of the non-aqueous vehicle and said sun-care product is substantially non-whitening upon application to wet skin.

15 Claims, No Drawings

CLEAR WET SPRAYS AND GELS

FIELD

The present application relates to sun-care products to protect keratinous substances from the damage of UV radiation, and more particularly, to sun-care products that can be applied on wet skin and/or hair without substantial clouding or whitening.

BACKGROUND

It is now generally accepted that ultraviolet (UV) radiation can be a serious health hazard. Even a limited exposure to solar radiation can cause short- and long-term skin damage, such as erythema, burns, wrinkles, lentigo ("liver spots"), skin cancers, keratotic lesions, and other cellular changes. There is a greater risk for developing such conditions for those who spend prolonged time in the sun, such as for their occupation or during recreation.

UV radiation is just one portion of the electromagnetic spectrum with wavelengths from about 100 nm and about 400 nm, and is further divided into three subregions. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns which may be harmful. The third subgroup, UV-C has the shortest wavelengths, from about 200 nm to about 290 nm, and the highest energy. The Earth's ozone layer effectively filters much UV-C radiation from reaching the ground. Nonetheless, UV-C rays can be generated from tanning bed devices.

In addition to harming the skin, UV radiation can injure the hair, resulting in color changes (especially for color-treated hair), embrittlement, and a loss in aesthetics (e.g., shine, manageability).

One approach to help reduce or prevent UV damage is the use of sun-care products that contain one or more UV actives. Sun-care products having one or more UV actives typically are applied on the skin, scalp, lips, and/or hair before and/or during exposure to UV radiation. (These products also are applied after exposure, for example, as part of a sun exposure remedy or daily care routine.) Swimming, rainfall, or even perspiration can washoff some of the sun-care product, so that reapplication may be recommended in these situation. These products may provided in the form of creams and lotions for the skin, and recently spray products have appeared that provide user convenience and efficacy. However, the application of sun-care products to wet skin presents its own challenges.

Sun-care products, especially those that apply clear on dry skin, typically run, drip, and/or turn cloudy/white when applied to wet skin. These effects are more than just cosmetic, as they can result in inconsistent, incomplete, or variable protection from UV damage, which is the very reason for product use. Hence, products are needed that substantially resolve these drawbacks.

Related disclosures include U.S. Pat. Nos. 4,193,989; 4,254,102; 4,486,405; 4,567,038; 5,026,540; 5,204,090; 5,223,250; 5,227,153; 5,587,148; 5,929,163; 6,007,799; 6,024,942; U.S. patent application publications 2002/0111387; 2004/0166070; 2004/0247550; 2004/126,336; 2006/0051384; 2008/0014155; international patent applications WO 2005/107693 and 2011/038120; German patent application DE 10 2004 029328; 199 26 671; Japanese patent JP 5311076; and U.K. patent GB 2404588

SUMMARY

The present application is directed to sun-care products that do not turn white, or run/drip when applied to wet skin. In accordance with one embodiment, the products are formulated to contain at least (A) a cosmetically-acceptable, substantially non-aqueous vehicle, and (B) one or more UV actives wherein the non-aqueous vehicle provides a combination of alcohol(s) and ester(s) sufficient to provide products that do not turn white or run/drip when applied to wet skin. In accordance with certain embodiments, the non-aqueous vehicle has a dielectric constant of 20 or less. In select embodiments, the non-aqueous vehicle has a dielectric constant of between about 15 and 20. A method for protecting keratinous substances from UV radiation also is provided.

In accordance with another aspect, sun-care products are disclosed that contain (A) 50% (w/w) or less of one or more alcohols, (B) one or more UV actives, and (C) a cosmetically-acceptable, substantially non-aqueous vehicle and the products do not turn white, or run/drip when applied to wet skin.

DETAILED DESCRIPTION

The present application is directed to sun-care products containing a synergistic blend of alcohol and esters to provide a composition that does not turn white, or run/drip when applied to wet skin. The products may be formulated to contain at least (A) a cosmetically-acceptable, substantially non-aqueous vehicle, and (B) one or more UV actives. In select embodiments, the non-aqueous vehicle has a dielectric constant of between about 15 and 20. A method for protecting keratinous substances from UV radiation also is provided.

Described herein are sun-care products that resolve problems noted with known and commercially-available products. The sun-care products described herein are substantially non-whitening when applied to wet skin, and comprise at least: (A) 50% (w/w) or less of one or more alcohols, (B) one or more UV actives, and (C) a cosmetically-acceptable, substantially non-aqueous vehicle.

Before considering various aspects of the invention, the following definitions first are provided.

The terms "ultraviolet" and "UV" refer to electromagnetic radiation, especially solar electromagnetic radiation, with a wavelength from about 100 nm to about 400 nm, and includes the UV-A, UV-B, and UV-C subclassifications of such radiation.

The term "UV-A" refers to ultraviolet electromagnetic radiation with a wavelength from about 320 nm to about 400 nm, and includes UV-A1 (from about 340 nm to about 400 nm) and UV-A2 (from about 320 nm to about 340 nm).

The term "UV-B" refers to ultraviolet electromagnetic radiation with a wavelength from about 290 nm to about 320 nm.

The term "UV-C" refers to ultraviolet electromagnetic radiation with a wavelength from about 200 nm to about 290 nm.

The term "UV active" refers to compositions that absorb, reflect, and/or scatter UV radiation.

The term "sun-care product" refers to personal care and/or pharmaceutical products comprising an effective amount of UV active(s). Sun-care products include beach and non-beach products that are applied to the face, décolleté, lips, and skin to treat and/or protect against erythema, burns, wrinkles, lentigo ("liver spots"), skin cancers, keratotic lesions, and cellular changes of the skin; and to hair to treat and/or protect against color changes, lack of luster, tangles, split ends, unmanageability, and embrittlement.

The term "keratinous substances" refers to substances having keratin. Examples of keratinous materials include skin, hair, lips, the scalp, and nails.

The term "vehicle" refers to compounds that can help carry, dissolve, disperse, and/or stabilize a formulation. Vehicles may be liquid (such as lower molecular weight alcohols, oils, and esters), semi-solid (such as waxes and polyalkylene oxides), and solids (such as polymers and higher molecular weight alcohols, oils, and esters).

For purposes of measuring the dielectric constant of the non-aqueous vehicle and calculating the ester content by weight of the non-aqueous vehicle, the non-aqueous vehicle described herein includes any alcohol in the formulation but does not take into consideration any polymer that may be present in the non-aqueous vehicle.

The term "in alphabetical order" refers to a list given with regard to the first letter of the entry, and does not construe any preference otherwise.

All percentages, ratio, and proportions used herein are based on a weight basis unless other specified.

A detailed description of different embodiments of the invention is now provided, followed by optional ingredients.

Alcohol(s)

Compositions according to the invention comprise at least one alcohol, which may serve to help dissolve, distribute, carry, and/or deliver the UV active(s) and/or co-ingredient(s) of the cosmetically-acceptable substantially non-aqueous vehicle.

Since many of the UV actives suitable for use in this invention are soluble in the cosmetically-acceptable, substantially non-aqueous vehicle, applicants have discovered that low concentrations of alcohol(s) find use. At low alcohol levels (or even no alcohol) the cosmetic vehicle can be formulated to dissolve, distribute, carry, and/or deliver the UV active(s). To improve the aesthetic qualities of the product, it may be desirable to use more than a low amount of the alcohol(s), particularly to impart elegant, smooth, and/or fast-drying characteristics.

In general, the amount of alcohol ranges from 1% (w/w) to 50% (w/w). A separate embodiment provides for sun-care products having from 20% (w/w) to 48% (w/w) ethanol, and in another embodiment this range is from about 30% (w/w) to 45% (w/w). Sun-care products having this amount of alcohol(s) were discovered not to turn white/cloudy when applied to wet skin, and is contrary to the overwhelming majority of products available on the market.

Examples of suitable alcohols include, without limitation: ethanol, 1-propanol, and 2-propanol. Some markets may allow methanol and/or denatured methanol, for example to denature ethanol, and so this alcohol also is contemplated.

UV Actives

The sun-care product formula also comprises at least one UV active. Examples of UV actives include: octyl salicylate (2-ethylhexyl salicylate, Escalol® 587); pentyl dimethyl PABA; octyl dimethyl PABA (padimate 0, Escalol® 507); benzophenone-1; benzophenone-6 (Uvinul® D-49); 2-(2H-benzotriazole-2-yl)-4,6-di-tert-pentylphenol (Uvinul® 3028); ethyl-2-cyano-3,3-diphenylacrylate (Uvinul® 3035); homomethyl salicylate (homosalate); bis-ethylhexyloxyphenol methoxyphenyl triazine (bemotrizinol, Escalol® S); methyl-(1,2,2,6,6-pentamethyl-4-piperidyl)-sebacate (Uvinul® 4092H); benzenepropanoic acid, 3,5-bis(1,1-dimethylethyl)-4-hydroxy-, C7-C9 branched alkyl esters (Irganox® 1135); 2-(2H-benzotriazole-2-yl)-4-methylphenol (Uvinul® 3033P); diethylhexyl butamido triazone (iscotrizinol, Uvasorb® HEB); amyl dimethyl PABA (lisadimate, glyceryl PABA); 4,6-bis(octylthiomethyl)-o-cresol (Irganox® 1520); CAS number 65447-77-0 (Uvinul® 5062H, Uvinul® 5062GR); red petroleum; ethylhexyl triazone (Uvinul® T-150); octocrylene (Escalol® 597); isoamyl-p-methoxycinnamate (amiloxate, Neo Heliopan® E1000); drometrizole; titanium dioxide; 2,4-di-tert-butyl-6-(5-chloro-2H-benzotriazole-2-yl)-phenol (Uvinul® 3027); 2-hydroxy-4-octyloxybenzophenone (Uvinul® 3008); benzophenone-2 (Uvinul® D-50); diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate (Irganox® 3052); drometrizole trisiloxane (Mexoryl® XL); menthyl anthranilate (meradimate); bis-(1,2,2,6,6-pentamethyl-4-piperidyl)-sebacate; butyl methoxydibenzoylmethane (avobenzone, Escalol® 517); 2-ethoxyethyl p-methoxycinnamate (cinnoxate); benzylidene camphor sulfonic acid (Mexoryl® SL); dimethoxyphenyl-[1-(3,4)]-4,4-dimethyl 1,3-pentanedione; zinc oxide.; N,N'-hexane-1,6-diyl-bis[3-(3,5-di-tert-butyl-4-hydroxyphenylpropionamide)] (Irganox® 1098); pentaerythritol tetrakis[3-(3,5-di-tert-butyl-4-hydroxyphenyl)propionate] (Irganox® 1010); 2,6-di-tert-butyl-4-[4,6-bis(octylthio)-1,3,5-triaziN-2-ylamino] phenol (Irganox® 565); 2-(2H-benzotriazole-2-yl)-4,6-bis(1-methyl-1-phenylethyl)phenol (Uvinul® 3034); trolamine salicylate (triethanolamine salicylate); diethylanolamine p-methoxycinnamate (DEA methoxycinnamate); polysilicone-15 (Parsol® SLX); CAS number 152261-33-1 (Uvinul® 5050H); 4-methylbenzylidene camphor (Eusolex® 6300, Parsol® 5000); bisoctrizole (Tinosorb® M); benzenamine, N-phenyl-, reaction products with 2,4,4-trimethylpentene (Irganox® 50507); sulisobenzone, Escalol® 577); (2-ethylhexyl)-2-cyano-3,3-diphenylacrylate (Uvinul® 3039); digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-; bis-(2,2,6,6-tetramethyl-4-piperidyl)-sebacate (Uvinul® 4077H); benzophenone-5 (sulisobenzone sodium); 1,3,5-tris(3,5-di-tert-butyl-4-hydroxybenzyl)-1,3,5-triazine-2,4,6(1H,3H,5H)-trione (Irganox® 3114); hexamethylendiamine (Uvinul® 4050H); benzophenone-8 (dioxybenzone); ethyl-4-bis(hydroxypropyl) aminobenzoate (roxadimate); 6-tert-butyl-2-(5-chloro-2H-benzotriazole-2-yl)-4-methylphenol (Uvinul® 3026); p-aminobenzoic acid (PABA); 3,3',3'',5,5',5''-hexa-tert-butyl-α-α'-α''-(mesitylene-2,4,6-triyl)tri-p-cresol (Irganox® 1130); lawsone with dihydroxyacetone; benzophenone-9 (Uvinul® DS-49); benzophenone-4 (sulisobenzone); ethylhexyl dimethoxy benzylidene dioxoimidazoline propionate; N,N'-bisformyl-N,N'-bis-(2,2,6,6-tetramethyl-4-piperidinyl)-; 3-benzylidene camphor (Mexoryl® SD); terephthalylidene dicamphor sulfonic acid; camphor benzalkonium methosulfate (Mexoryl® SO); bisdisulizole disodium (Neo Heliopan® AP); etocrylene; ferulic acid; 2-(2H-benzotriazole-2-yl)-4-(1,1,3,3-tetramethylbutyl)-phenol (Uvinul® 3029); ecamsule (Mexoryl® SX); 4,6-bis(dodecylthiomethyl)-o-cresol (Irganox® 1726); beta-2-glucopyranoxy propyl hydroxy benzophenone; phenylbenzimidazole sulfonic acid (ensulizole, Eusolex® 232, Parsol® HS); benzophenone-3 (oxybenzone, Escalol® 567); diethylamine hydroxybenzoyl hexylbenzoate (Uvinul® A Plus); 3',3'-diphenylacryloyl)oxy]methyl}-propane (Uvinul® 3030); and ethylhexyl p-methoxycinnamate (Escalol® 557).

It is recognized that the availability of UV absorbers in sun-care compositions often depends on local regulatory laws; hence, the above list may include UV absorbers that are not allowed in certain regions.

The amount of any one of the UV actives may vary from 0.1% (w/w) to 40% (w/w) of the sun-care product formulation. In general, however, the type and amount of the UV active(s) may be selected to impart a desired sun protection factor (SPF) and/or UV-A protection to the sun-care product. For example, increasing SPF generally requires an increase in the addition level of UV active(s), or the use of more efficient active(s). Embodiments of the invention provide for sun-care products having an SPF of 15, 30, 50, and 70. Given the above discussion, it is trivial to formulate lower SPF products, e.g., SPF of 4 or 8, from specific embodiments.

Various national agencies have set limits on maximum UV active concentrations, so the allowable addition level may be less than 40% (w/w). As an illustration of this point, the monograph *The Encyclopedia of Ultraviolet Filters* (2007), which is hereby incorporated in its entirety by reference, indicates which UV actives are allowed in different countries, as well as the highest allowable addition levels. The direct conclusion is that these levels have not been harmonized worldwide. With this understanding and the need for sun-care products having varying degrees of UV-A and/or UV-B protection, a separate embodiment provides for sun-care products having from about 1% (w/w) to about 25% (w/w) of one or more UV active(s).

In certain embodiments the one or more UV active(s) is selected from the following (in alphabetical order): 4-methylbenzylidene camphor, avobenzone, bemotrizinol, benzophenone-1, benzophenone-2, benzophenone-3 (oxybenzone), benzophenone-4 (sulisobenzone), benzophenone-5 (sulisobenzone sodium), benzophenone-6, benzophenone-8 (dioxybenzone), benzophenone-9, benzylidene camphor sulfonic acid, bisdisulizole disodium, bisoctrizole, camphor benzalkonium methosulfate, cinoxate, DEA methoxycinnamate, diethylamine hydroxybenzoyl hexylbenzoate, digalloyl trioleate, diisopropyl methylcinnamate, dimethoxyphenyl-[1-(3,4)]-4,4-dimethyl 1,3-pentanedione, drometrizole, drometrizole trisiloxane, ecamsule, ensulizole, ethylhexyl p-methoxycinnamate, ethylhexyl triazone, ferulic acid, glyceryl ethylhexanoate dimethoxycinnamate, homomethyl salicylate (homosalate), iscotrizinol, isoamyl-p-methoxycinnamate, lisadimate, meradimate, camphor benzalkonium methosulfate, octocrylene, octyl dimethyl PABA (padimate O), octyl salicylate (octisalate), p-aminobenzoic acid (PABA), PEG-25 PABA, pentyl dimethyl PABA (padimate A), polysilicone-15, roxadimate, titanium dioxide, trolamine salicylate, and zinc oxide.

It may be beneficial and/or desirable to formulate the sun-care product with more than one UV active. The reasons for such a formulary strategy are many, and include cost, manufacturing, and product performance considerations. Regarding the latter, blends of two or more UV actives may help extend the range of UV radiation absorption provided by the sun-care product, especially to cover the various UV-A and UV-B designations of UV radiation. Through using satisfactory blends, sun-care products can be formulated to provide partial or even complete UV protection. In one embodiment, protection from UV-A wavelengths is achieved by the use of avobenzone, ecamsule, titanium dioxide, and/or zinc oxide, each of which may be used in combination with other UV-A and/or UV-B actives.

In yet another embodiment, suitable combinations of UV absorbers that can be used include, without limit or restriction:
avobenzone and ecamsule,
avobenzone and ensulizole,
avobenzone and oxybenzone,
avobenzone and zinc oxide,
ensulizole and octinoxate,
octinoxate and oxybenzone,
titanium dioxide and zinc oxide,
avobenzone, oxybenzone, homosalate, and octisalate,
avobenzone, oxybenzone, homosalate, octisalate, and octocrylene, and
octinoxate, octisalate, octocrylene, oxybenzone, and zinc oxide.

Cosmetically-Acceptable, Substantially Non-Aqueous Vehicle

The sun-care products according to the present application also comprise a cosmetically-acceptable, substantially non-aqueous vehicle, which may assist in dissolving, distributing, carrying, delivering, adhering, and/or maintaining the sun-care product on the keratinous substrate. This vehicle also may impart varying degrees of water fastness, water proofness, and/or water repellency, and/or enable film permeability (for examples, for water vapor, oxygen). For some applications, it may be desirable to select this vehicle to impart shine, smooth skin-feel, hair manageability, and/or hair conditioning.

The amount of this vehicle in the sun-care product formula depends on the quantity of alcohol(s) and UV active(s) employed. Generally speaking, the vehicle represents from 50% (w/w) to 99% (w/w) of the total formula.

Accordingly, the vehicle comprises one or more esters, glycol, hydrocarbons, oils, polymers, and they may be used in various combinations. These vehicle constituents are well-known to one of ordinary skill in the art, and the assorted types and use levels can be found in trade brochures, cosmetic handbooks, and patent literature. Many examples of these constituents can be found in the following references, each of which is herein incorporated in its entirety by reference: "Inventory and common nomenclature of ingredients employed in cosmetic products," *Official Journal of the European Union*, 5.4.2006, pages L 97/1 through L 97/528; and *International Cosmetic Ingredient Dictionary and Handbook*, 13$^{th}$ edition, ISBN: 1882621476, published by The Personal Care Products Council in January 2010. Representative, but non-limiting examples are provided after a note concerning water content.

Any of these materials may have associated with it absorbed and/or adsorbed water, which can be carried into the otherwise substantially anhydrous formula. For economic, sourcing, and/or formulation reasons, it may be disadvantageous to process hygroscopic materials to make them completely free of water. Therefore, consistent with its meaning in the art, the phrase "substantially anhydrous" means having 10% (w/w) or less water. In one embodiment the formula comprises 2% (w/w) or less total water, and in another particular embodiment the formula comprises 1% (w/w) or less total water.

Examples of suitable esters include the following products sold by Ashland Specialty Ingredients: cetyl lactate (Ceraphyl® 28), lauryl lactate (Ceraphyl® 31), C12-C15 alkyl lactate (Ceraphyl® 41), dioctyl malate (Ceraphyl® 45), myristyl lactate (Ceraphyl® 50), tridecyl neopentanoate (Ceraphyl® 55), decyl oleate (Ceraphyl® 140), isodecyl neopentanoate (Ceraphyl® 140A), diisopropyl adipate (Ceraphyl® 230), ethylhexyl palmitate (Ceraphyl® 368), isostearyl neopentanoate (Ceraphyl® 375), myristyl myristate and myristyl laurate (Ceraphyl® 424), isocetyl stearate (Ceraphyl® 494), isocetyl stearoyl stearate (Ceraphyl® 791), octyldodecyl stearoyl stearate (Ceraphyl® 847), octyldodecyl stearate (Ceraphyl® ODS), castoryl maleate (Ceraphyl® RMT), isodecyl neopentanoate (Ceraphyl® SLK), and glyceryl stearate (Cerasynt® SD).

Additional examples of suitable esters include the following lactates: butyl lactate, C12-C13 alkyl lactate, C12-C15 alkyl lactate, chitosan lactate, dimethiconol lactate, ethyl hydroxypicolinium lactate, ethyl lactate, glycereth-7 lactate, glyceryl citrate/lactate/linoleate/oleate, glyceryl palmitate lactate, glyceryl stearate lactate, hydrogenated tallow glyceride lactate, isostearyl lactate, lactoyl methylsilanol elastinate, lauryl lactate, linoleyl lactate, methyl hydroxycetyl glucaminium lactate, myristyl lactate, octyldodecyl lactate, oleyl lactate, sodium lactate, sodium stearoyl lactylate, stearyl lactate, TEA-lactate, and trilactin.

Other examples of suitable esters include the following stearates: acetylated glycol stearate, acetylated sucrose distearate, ammonium isostearate, arachidyl glycol isostearate, batyl isostearate, behenyl isostearate, butyl isostearate, butyl stearate, C11-C15 pareth-3 stearate, C11-C15 pareth-12 stearate, C16-C36 alkyl stearate, C18-C20 glycol isostearate, C18-C38 alkyl hydroxystearoyl stearate, C30-050 alkyl stearate, C40-C60 alkyl stearate, cetearyl stearate, cetyl glycol isostearate, cetyl stearate, chimyl isostearate, chimyl stearate, cholesteryl isostearate, cholesteryl stearate, decyl isostearate, dextrin stearate, diglyceryl stearate malate, dihydrocholesteryl isostearate, dimethicone copolyol hydroxystearate, dimethicone copolyol isostearate, dimethicone copolyol stearate, dimethicone hydroxystearate, dimethicone isostearate, dimethiconol stearate, dimethyl lauramine isostearate, dipentaerythrityl hexahydroxysterate, dipentaerythrityl hexahydroxysterate/isostearate, dipentaerythrityl hexahydroxysterate/stearate/rosinate, ethyl isosterate, ethyl stearate, ethylhexyl acetoxystearate, ethylhexyl hydroxystearate, ethylhexyl isostearate, ethylhexyl stearate, glycereth-8 hydroxystearate, glycereth-20 stearate, glycereth-25 PCA isostearate, glyceryl dihydroxystearate, glyceryl diisostearate, glyceryl distearate, glyceryl ethylhexanoate/stearate/adipate, glyceryl hydroxystearate, glyceryl isostearate, glyceryl isostearate/myristate, glyceryl isostearates, glyceryl palmitate/stearate, glyceryl stearate, glyceryl stearate citrate, glyceryl stearate diacetate, glyceryl stearate lactate, glyceryl stearate succinate, glyceryl stearate acetate, glyceryl stearate/maleate, glyceryl triacetyl hydroxystearate, glyceryl/sorbitol oleate/hydroxystearate, glycol distearate, glycol hydroxystearate, glycol stearate, glycolamide stearate, glycyrrhentinyl stearate, hexacosyl glycol isostearate, hexanediol distearate, hexyl isostearate, hexyldecyl isostearate, hexyldecyl stearate, hydroxycetyl isostearate, hydroxyoctacosanyl hydroxystearate, isobutyl stearate, isocetyl isostearate, isocetyl linoleoyl stearate, isocetyl stearate, isostearoyl stearate, isodecyl hydroxystearate, isodecyl stearate, isopropyl hydroxystearate, isopropyl isostearate, isopropyl stearate, isosteareth-10 stearate, isostearoyl isostearyl stearate, isostearoyl stearyl stearate, lauryl isostearate, lauryl stearate, methyl glucose isostearate, methyl glucose sesquiisostearate, methyl glucose sesquiisostearate, methyl hydroxystearate, methyl isostearate, methyl stearate, myristyl isostearate, myristyl stearate, neopentyl glycol diisostearate, octasanyl glycol isostearate, octyldodecyl hydroxystearate, octyldodecyl isostearate, octyldodecyl stearate, octyldodecyl stearoyl stearate, oleyl stearate, PEG-y diisostearate (wherein y is a number from 2 to 200), PEG-y distearate (wherein y is a number from 2 to 200), PEG-y isostearate (wherein y is a number from 2 to 200), PEG-y stearate (wherein y is a number from 2 to 200), pentaerythrityl isostearate/caprate/caprylate/adipate, pentaerythrityl stearate, pentaerythrityl stearate/caprate/caprylate adipate, pentaerythrityl stearate/isostearate/adipate/hydroxystearate, pentaerythrityl tetrastearate, polyglyceryl-2 dipolyhydroxystearate, polyglyceryl-2 distearate, polyglyceryl-2 isostearate, polyglyceryl-3 triisostearate, polyglyceryl-4 pentastearate, polyglyceryl-4 tristearate, potassium stearate, PPG-2 isostearate, PPG-15 isostearate, PPG-15 stearate, PPG-20 methyl glucose ether distearate, propylene glycol diisostearate, propylene glycol distearate, propylene glycol hydroxystearate, propylene glycol stearate, sodium stearate, sorbitan distearate, steareth-5 stearate, stearyl glycol isostearate, stearyl stearate, stearyl stearoyl stearate, sucrose distearate, sucrose polystearate, sucrose stearate, sucrose tetrastearate triacetate, sucrose tristearate, tetradecyleicosyl stearate, tridecyl stearate, tridecyl stearoyl stearate, trimethylolpropane triisostearate, trimethylolpropane tristearate, and glycerol tristearate. Combinations of any of these esters may be used.

The cosmetically-acceptable, substantially non-aqueous vehicle also may comprise one or more glycols, including: propylene glycol, butylene glycol, hexylene glycol, diethylene glycol, dipropylene glycol, polyethylene glycol, glycerin, and mixtures thereof.

The vehicle also may comprise one or more hydrocarbons, such as: cera microcrystallina, a C9-C12 aliphatic hydrocarbon, a C9-C12 isoparaffin, isododecane, isoeicosane, isohexadecane, a microcrystalline wax, mineral spirits, paraffin, paraffinum liquidum, petrolatum, petroleum distillates, red petroleum, synthetic wax. Blends of these materials may be used.

The vehicle also may comprise one or more oils. Useful oils include those oils from plant, animal, and synthetic origins, such as sunflower oil, corn oil, soy oil, avocado oil, jojoba oil, squash oil, raisin seed oil, sesame seed oil, walnut oils oil, glycerol tricaprocaprylate, Purcellin oil, jojoba oil, eucalyptus oil, lavender oil, vetiver oil, litsea cubeba oil, lemon oil, sandalwood oil, rosemary oil, chamomile oil, savory oil, nutmeg oil, cinnamon oil, hyssop oil, caraway oil, orange oil, geranium oil, cade oil, oil of bergamot, hexadecane, oil of paraffin, and combinations thereof.

Synthetic oils also are known and include the following materials: polyolefins such as polybutene, polyisobutene, and polydecenes. Also suitable are the various silicone oils, being polymerized siloxanes that are the silicon-based analogues of carbon-based compounds. This concept of silicone oils includes polyorganosiloxanes, being siloxanes with one or more organic chains. Examples of silicone oils are, without limitation, C24-C28 alkyl methicone (CAS no. 158061-44-0), C30-C45 alkyl methicone (CAS no. 246864-88-0), the many compounds having "dimethicone" in their INCI name (e.g., cetyl dimethicone, cetyl dimethicone copolyol, dimethicone bis-aminohydroxypropyl copolyol, dimethicone copolyol), the many compounds having "dimethiconol" in their INCI name (e.g., dimethiconol, dimethiconol beeswax, dimethiconol behenate), the many compounds having "methylsilanol" in their INCI name (e.g., methylsilanol carboxymethyl theophylline alginate, methylsilanol elastinate, methylsilanol spirulinate), polysilicones 1 through 11, and silicone quaterniums 1 through 13. Combinations of these oils may be used.

The cosmetic vehicle also may comprise one or more polymers. Many suitable polymers are known in the art, and include the following examples (without restriction): acrylate/t-octylpropenamide copolymer, acrylates/octylacrylamide copolymer, acrylates/C12-C22 alkyl methacrylate crosspolymer, adipic acid/diethylene glycol/glycerin crosspolymer (Lexorez® 100), bis-stearyl ethylenediamine/neopentyl glycol/stearyl hydrogenated dimer dilinoleate copolymer (Sylvaclear® C75V4), carbomer, cetyl dimethicone bis-vinyl dimethicone crosspolymer (Silwax® CR-05016), ethylenediamine/hydrogenated dimer dilinoleate copolymer bis-di-C14-18 alkyl amide (Sylvaclear® A200V10, A2614V), octadecene/MA copolymer, octylacrylamide/acrylate/butylaminoethyl methacrylate copolymer ('090), octyldodecyl citrate crosspolymer, PEG 10/15 crosspolymer, PEG 12 dimethicone crosspolymer, polyamide-3 (Sylvaclear® WF1500V, AF1200V, AF1900V, PE1800V), polyester-5 (Eastman AQ 38S, 48, 55S), polyester-7 and neopentyl glycol diheptanoate (LexFilm® Sun), polyester-10 and propylene glycol dibenzoate (LexFilm® Spray), polyimide-4 (Sylvaclear® WF1500V), polyimide-6 (Sylvaclear® PE400V), PVP/hexadecene copolymer, silicone-polyamide copolymer, stearyl hydrogenated dimer dilionleate copolymer, styrene acrylates copolymer, tetrapolymer of methacrylic acid, methyl methacrylate, butyl acrylate, and cetyleicosinyl methacrylate, trimethylpentanediol/adipic acid copolymer (Lexorez® TL-8), trimethylpentanediol/adipic acid/glycerin crosspolymer (Lexorez® 200), VA/butyl maleate/isobornyl acrylate copolymer, VCL/VP/DMAEMA copolymer (Advantage® S, Advantage HC-37), VCL/VP/DMAEMA (and) lauryl pyrrolidone (Advantage LC-E), polyquaternium-69 (Aquastyle™ 300), VP/VCL/DMAPA acrylates copolymer (Aquaflex® SF-40), imidized isobutylene/ethylmaleimide/hydroxyethylmaleimide copolymer (Aquaflex® FX-64), polyimide-1 (Aquaflex® XL-30), VP/DMAEMA copolymer, polyquaternium-11 (Gafquat®), polyquaternium-28 (Gafquat® HS-100), ethyl ester of PVM/MA copolymer (Gantrez® SP-215, Gantrez® ES-225, Omnirez® 2000), butyl ester of PVM/MA copolymer (Gantrez® A-425, ES-425, ES-435), isopropyl ester of PVM/MA copolymer (Gantrez® ES-335), PVP, PVP/VA copolymer, VP/DMAPA acrylates copolymer (Styleze® CC-10), VP/acrylates/lauryl methacrylate copolymer (Styleze® 2000), polyquaternium-5 (Styleze® W), PVP (and) dimethicone, polyquaternium (and) dimethicone (Gafquat® HSi), VP/hexadecene copolymer (Antaron® V-216), VP/eicosene copolymer (Antaron® V-220F), and triacontanyl PVP (Antaron® WP-660). Also suitable are cellulose polymers, which include guar hydroxypropyltrimonium chloride (AquaCat™), carboxymethylcellulose (Aqualon™), methylcellulose and hydroxypropylmethyl cellulose (Benecel™), sodium carboxymethyl cellulose (Blanose™), hydroxypropylcellulose (Klucel™), hydroxyethylcellulose (Natrosol™), cetyl-modified hydroxyethylcellulose (Natrosol™ Plus), cationic guar (N-Hance™), all of which are offered for sale by Ashland Specialty Ingredients.

The non-aqueous vehicle in accordance with certain embodiments contains at least about 10%, more particularly about 15%-50%, and in some cases from about 18%-30% esters by weight based on the total weight of the non-aqueous vehicle (including any alcohol(s)). In accordance with certain embodiments, the non-aqueous vehicle comprises a mixture of alcohol and esters that provides for a sun-care product that is substantially non-whitening upon application to wet skin. The non-aqueous vehicle may be formulated to provide a dielectric constant of 20 or less, more particularly about 15-20, for the non-aqueous vehicle. For purposes of the foregoing calculations, any polymers are not included in determining the total weight of the non-aqueous vehicle or the dielectric constant for the non-aqueous vehicle.

The sun-care product formulas also may comprise one or more additives, including those used in the skin-care or sun-care markets. Examples of these additives include (in alphabetical order): aloe vera, an anti-bacterial agent, an anti-fungal agent, anti-viral agent, beeswax, camellia oleifera leaf extract, cedar oil, citronella oil, coco butter, DEET, dihydroxyacetone, fragrance, geraniol oil, lemon eucalyptus oil, mango butter, neem oil, peppermint oil, a peptide, picaridin, piperonyl butoxide, pyrethrum, a vitamin A, vitamin C, a vitamin E, a vitamin B, and combinations thereof.

Useful pharmaceutical active agents may be conjointly administered according to the present invention include antimicrobial drugs: antibacterials, antifungals, antiprotozoans, and antivirals. Examples of these materials include acceptable salts of β-lactam drugs, amanfadine, amikacin, capreomycin, chlorhexidine, chlortetracycline, ciprofioxacin, clindamycin, doxycycline, erythromycin, ethambutol, gentamicin, kanamycin, lineomycin, methacycline, methenamine, metronidazole, miconazole, minocycline, neomycin, netilmicin, norfioxacin, oxytetracycline, paramomycin, pentamidine, quinolone drugs, streptomycin, tetracycline, tobramycin, and triclosan.

EXAMPLES

Comparative Example 1

An anhydrous, spray sunscreen was prepared having the formula shown in Table 1. When it was sprayed onto wet skin, the sunscreen turned milky-white.

TABLE 1

The anhydrous, spray sunscreen of Comparative Example 1

| ingredient | trade name | addition level, 114-1 (parts by weight) |
|---|---|---|
| VA/butyl maleate/isobornyl acrylate copolymer | Advantage ® Plus | 2.0 |
| ethanol | | 61.0 |
| avobenzone | Escalol ® 517 | 3.0 |
| oxybenzone | Escalol ® 567 | 6.0 |
| octocrylene | Escalol ® 597 | 8.0 |
| homosalate | Eusolex ® HMS | 15.0 |
| octisalate | Escalol ® 587 | 5.0 |
| total | | 100.0 |

Example 1

An anhydrous, spray sunscreen was prepared having the same ingredients as Comparative Example 1, but with a lower amount of ethanol (Table 2). The balance was made by adding two esters, diisopropyl adipate and phenethyl benzoate, to the formula. It was sprayed onto wet skin and remained clear

TABLE 2

The anhydrous, spray sunscreen of Example 1

| ingredient | trade name | addition level (parts by weight) 114-2 |
|---|---|---|
| sub-formulation I | | |
| ethanol | | 41.0 |
| VA/butyl maleate/isobornyl acrylate copolymer | Advantage ® Plus | 2.0 |
| sub-formulation II | | |
| avobenzone | Escalol ® 517 | 3.0 |
| oxybenzone | Escalol ® 567 | 6.0 |
| homosalate | Eusolex ® HMS | 15.0 |

TABLE 2-continued

The anhydrous, spray sunscreen of Example 1

| ingredient | trade name | addition level (parts by weight) 114-2 |
|---|---|---|
| octisalate | Escalol ® 587 | 5.0 |
| octocrylene | Escalol ® 597 | 8.0 |
| sub-formulation III | | |
| diisopropyl adipate | Ceraphyl ® 230 | 10.0 |
| phenethyl benzoate | X-Tend ® 226 | 10.0 |
| total | | 100.0 |

Ester content = 32.8% of non-aqueous vehicle

Example 2

Three anhydrous, water-resistant spray sunscreens were made having the ingredients and addition levels shown in Table 3. These sunscreens had a theoretical sun protection factor (SPF) of 30.

All three sunscreens remained clear after spraying onto wet skin.

TABLE 3

The anhydrous, spray sunscreens of Example 2

| ingredient | trade name | 120-1 | 120-2 | 120-3 |
|---|---|---|---|---|
| sub-formulation I | | | | |
| ethanol | | 38.0 | 39.0 | 40.0 |
| VA/butyl maleate/isobornyl acrylate copolymer | Advantage ® Plus | 2.0 | | |
| acrylates/octylacrylamide copolymer | Dermacryl ® 79 | | 1.0 | |
| sub-formulation II | | | | |
| avobenzone | Escalol ® 517 | 2.0 | 2.0 | 2.0 |
| oxybenzone | Escalol ® 567 | 4.0 | 4.0 | 4.0 |
| homosalate | Eusolex ® HMS | 15.0 | 15.0 | 15.0 |
| octisalate | Escalol ® 587 | 5.0 | 5.0 | 5.0 |
| sub-formulation III | | | | |
| diisopropyl adipate | Ceraphyl ® 230 | 12.0 | 12.0 | 12.0 |
| isodecyl neopentanoate | Ceraphyl ® SLK | 14.0 | 14.0 | 14.0 |
| isostearyl neopentanoate | Ceraphyl ® 375 | 8.0 | 8.0 | 8.0 |
| total | | 100.0 | 100.0 | 100.0 |

Ester content = 45.9%-47.2% of non-aqueous vehicle

Example 3

The ethanol content of sunscreen formula 120-1 of Example 2 was increased (Table 4) to determine the maximum amount before the sunscreen turned white when sprayed on wet skin. The theoretical SPF value for these sunscreens also was 30.

Formula 126-1 sprayed clear on wet skin, and 126-2 (with 45% ethanol) exhibited minimal whitening.

TABLE 4

The anhydrous, spray sunscreens of Example 3

| ingredient | trade name | 126-1 | 126-2 |
|---|---|---|---|
| sub-formulation I | | | |
| ethanol | | 40.0 | 45.0 |
| VA/butyl maleate/isobornyl acrylate copolymer | Advantage ® Plus | 2.0 | 2.0 |
| sub-formulation II | | | |
| avobenzone | Escalol ® 517 | 2.0 | 2.0 |
| oxybenzone | Escalol ® 567 | 4.0 | 4.0 |
| homosalate | Eusolex ® HMS | 15.0 | 15.0 |
| octisalate | Escalol ® 587 | 5.0 | 5.0 |
| sub-formulation III | | | |
| diisopropyl adipate | Ceraphyl ® 230 | 11.0 | 9.5 |
| isodecyl neopentanoate | Ceraphyl ® SLK | 13.0 | 11.0 |
| isostearyl neopentanoate | Ceraphyl ® 375 | 8.0 | 6.5 |
| total | | 100.0 | 100.0 |

Ester content = 37.5-44.4% of non-aqueous vehicle

Example 4

The anhydrous, water-resistant spray sunscreens of Example 2 were modified to contain higher levels of UV actives (Table 5). The sunscreens had a theoretical SPF of 50.

All three sunscreens remained white after spraying onto wet skin.

TABLE 5

The anhydrous, spray sunscreens of Example 4

| ingredient | trade name | 115-1 | 115-2 | 115-3 |
|---|---|---|---|---|
| sub-formulation I | | | | |
| ethanol | | 39.0 | 40.0 | 41.0 |
| VA/butyl maleate/isobornyl acrylate copolymer | Advantage ® Plus | 2.0 | | |
| acrylates/octylacrylamide copolymer | Dermacryl ® 79 | | 1.0 | |
| sub-formulation II | | | | |
| avobenzone | Escalol ® 517 | 3.0 | 3.0 | 3.0 |
| oxybenzone | Escalol ® 567 | 6.0 | 6.0 | 6.0 |
| homosalate | Eusolex ® HMS | 15.0 | 15.0 | 15.0 |
| octisalate | Escalol ® 587 | 5.0 | 5.0 | 5.0 |
| octocrylene | Escalol ® 597 | 8.0 | 8.0 | 8.0 |
| sub-formulation III | | | | |
| diisopropyl adipate | Ceraphyl ® 230 | 10.0 | 10.0 | 10.0 |
| isodecyl neopentanoate | Ceraphyl ® SLK | 12.0 | 12.0 | 12.0 |
| total | | 100.0 | 100.0 | 100.0 |

Example 5

Two SPF 50 formulas were prepared with varying levels of ethanol (Table 6) to determine how much of the alcohol could be incorporated before the formulas whitened when sprayed on wet skin. The proportions of the other ingredients remained constant.

Both formulas remained clear when sprayed on wet skin up to (and including) 45% ethanol.

TABLE 6

The ethanol spray sunscreens of Example 5

| ingredient | trade name | addition level (parts by weight) 121-1 | 121-3 |
|---|---|---|---|
| sub-formulation I | | | |
| ethanol | | 45.0 | 42.0 |
| VA/butyl maleate/isobornyl acrylate copolymer | Advantage ® Plus | 2.0 | 2.0 |
| sub-formulation II | | | |
| avobenzone | Escalol ® 517 | 3.0 | 3.0 |
| oxybenzone | Escalol ® 567 | 6.0 | 6.0 |
| homosalate | Eusolex ® HMS | 15.0 | 15.0 |
| octisalate | Escalol ® 587 | 5.0 | 5.0 |
| octocrylene | Escalol ® 597 | 8.0 | 8.0 |
| sub-formulation III | | | |
| diisopropyl adipate | Ceraphyl ® 230 | 7.0 | 8.5 |
| isodecyl neopentanoate | Ceraphyl ® SLK | 9.0 | 10.5 |
| total | | 100.0 | 100.0 |

Ester content = 26.2%-31.1% of non-aqueous vehicle

Comparative Example 2

An SPF 50 formula was made having 50% ethanol (Table 7), more than the formulas of Example 5.

This formula turned white when applied to wet skin.

TABLE 7

The ethanol sunscreens of Comparative Example 2

| ingredient | trade name | addition level (parts by weight) 121-2 |
|---|---|---|
| sub-formulation I | | |
| ethanol | | 50.0 |
| VA/butyl maleate/isobornyl acrylate copolymer | Advantage ® Plus | 2.0 |
| sub-formulation II | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 8.0 |
| sub-formulation III | | |
| diisopropyl adipate | Ceraphyl ® 230 | 4.5 |
| isodecyl neopentanoate | Ceraphyl ® SLK | 6.5 |
| total | | 100.0 |

Example 6

The SPF 50 formula 115-2 of Example 4 was modified to contain both VA/butyl maleate/isobornyl acrylate copolymer and acrylates/octylacrylamide copolymer (Table 8).

The formula remained clear when sprayed on wet skin.

TABLE 8

The anhydrous, spray sunscreens of Example 6

| ingredient | trade name | addition level (parts by weight) 130-1 |
|---|---|---|
| sub-formulation I | | |
| ethanol | | 38.0 |
| VA/butyl maleate/isobornyl acrylate copolymer | Advantage ® Plus | 2.0 |
| acrylates/octylacrylamide copolymer | Dermacryl ® 79 | 1.0 |
| sub-formulation II | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 8.0 |
| sub-formulation III | | |
| diisopropyl adipate | Ceraphyl ® 230 | 10.0 |
| isodecyl neopentanoate | Ceraphyl ® SLK | 12.0 |
| total | | 100.0 |

Example 7

Two formulas were made, one having polydimethylsiloxane (Table 9), which can enhance film permeability to gases (e.g., water vapor, oxygen), and consequently, skin respiration.

Both sunscreens remained clear after spraying on wet skin.

TABLE 9

The anhydrous, spray sunscreens of Example 7

| ingredient | trade name | addition level (parts by weight) 132-1 | 132-2 |
|---|---|---|---|
| sub-formulation I | | | |
| ethanol | | 40.0 | 40.0 |
| VA/butyl maleate/isobornyl acrylate copolymer | Advantage ® Plus | 2.0 | 2.0 |
| sub-formulation II | | | |
| avobenzone | Escalol ® 517 | 3.0 | 3.0 |
| oxybenzone | Escalol ® 567 | 6.0 | 6.0 |
| homosalate | Eusolex ® HMS | 15.0 | 15.0 |
| octisalate | Escalol ® 587 | 5.0 | 5.0 |
| octocrylene | Escalol ® 597 | 10.0 | 10.0 |
| sub-formulation III | | | |
| diisopropyl adipate | Ceraphyl ® 230 | 8.5 | 6.0 |
| isodecyl neopentanoate | Ceraphyl ® SLK | 10.5 | 8.0 |
| polydimethylsiloxane | Wacker-Belsil ® DM5 | | 5.0 |
| total | | 100.0 | 100.0 |

Example 8

The three anhydrous, spray sunscreens of Example 4 were modified by increasing the amount of octocrylene (Table 10) in order to increase the SPF to a theoretical value of 70.

All three sunscreens remained clear after spraying onto wet skin.

TABLE 10

The anhydrous, spray sunscreens of Example 8

| ingredient | trade name | addition level (parts by weight) | | |
|---|---|---|---|---|
| | | 118-1 | 118-2 | 118-3 |
| sub-formulation I | | | | |
| ethanol | | 37.0 | 38.0 | 39.0 |
| VA/butyl maleate/isobornyl acrylate copolymer | Advantage ® Plus | 2.0 | | |
| acrylates/octylacrylamide copolymer | Dermacryl ® 79 | | 1.0 | |
| sub-formulation II | | | | |
| avobenzone | Escalol ® 517 | 3.0 | 3.0 | 3.0 |
| oxybenzone | Escalol ® 567 | 6.0 | 6.0 | 6.0 |
| homosalate | Eusolex ® HMS | 15.0 | 15.0 | 15.0 |
| octisalate | Escalol ® 587 | 5.0 | 5.0 | 5.0 |
| octocrylene | Escalol ® 597 | 10.0 | 10.0 | 10.0 |
| sub-formulation III | | | | |
| diisopropyl adipate | Ceraphyl ® 230 | 10.0 | 10.0 | 10.0 |
| isodecyl neopentanoate | Ceraphyl ® SLK | 12.0 | 12.0 | 12.0 |
| total | | 100.0 | 100.0 | 100.0 |

Example 9

The SPF 70 (theoretical) sunscreen of Example 8 was reformulated with: (a) a higher amount of the VA/butyl maleate/isobornyl acrylate copolymer to impart greater water repellency on skin, or (b) by adding hexylene glycol to (Table 11).

Both sunscreens were clear after spraying onto wet skin. Due to the formulation changes these sprayed sunscreen left a sheen on wet skin and improved water repellency.

TABLE 11

The anhydrous, spray sunscreens of Example 9

| ingredient | trade name | addition level (parts by weight) | |
|---|---|---|---|
| | | 122-1 | 122-2 |
| sub-formulation I | | | |
| ethanol | | 35.0 | 37.0 |
| VA/butyl maleate/isobornyl acrylate copolymer | Advantage ® Plus | 4.0 | 2.0 |
| sub-formulation II | | | |
| avobenzone | Escalol ® 517 | 3.0 | 3.0 |
| oxybenzone | Escalol ® 567 | 6.0 | 6.0 |
| homosalate | Eusolex ® HMS | 15.0 | 15.0 |
| octisalate | Escalol ® 587 | 5.0 | 5.0 |
| octocrylene | Escalol ® 597 | 10.0 | 10.0 |
| sub-formulation III | | | |
| diisopropyl adipate | Ceraphyl ® 230 | 10.0 | 9.0 |
| isodecyl neopentanoate | Ceraphyl ® SLK | 12.0 | 11.0 |
| hexylene glycol | | | 2.0 |
| total | | 100.0 | 100.0 |

Example 10

Formula 118-1 of Example 9 was studied to determine the maximum ethanol content before the sprayed sunscreen turned white on wet skin (Table 12).

The maximum ethanol level in these formulas was found to be 45% before they turn white when sprayed on wet skin.

TABLE 12

The anhydrous, spray sunscreens of Example 10

| ingredient | trade name | addition level (parts by weight) | | |
|---|---|---|---|---|
| | | 123-1 | 123-3 | 123-2 |
| sub-formulation I | | | | |
| ethanol | | 40.0 | 43.0 | 45.0 |
| VA/butyl maleate/isobornyl acrylate copolymer | Advantage ® Plus | 2.0 | 2.0 | 2.0 |
| sub-formulation II | | | | |
| avobenzone | Escalol ® 517 | 3.0 | 3.0 | 3.0 |
| oxybenzone | Escalol ® 567 | 6.0 | 6.0 | 6.0 |
| homosalate | Eusolex ® HMS | 15.0 | 15.0 | 15.0 |
| octisalate | Escalol ® 587 | 5.0 | 5.0 | 5.0 |
| octocrylene | Escalol ® 597 | 10.0 | 10.0 | 10.0 |
| sub-formulation III | | | | |
| diisopropyl adipate | Ceraphyl ® 230 | 8.5 | 7.0 | 6.0 |
| isodecyl neopentanoate | Ceraphyl ® SLK | 10.5 | 9.0 | 8.0 |
| total | | 100.0 | 100.0 | 100.0 |

Example 11

Two SPF-70 sunscreens were prepared (Table 13) to determine the effect of the VA/butyl maleate/isobornyl acrylate copolymer on measured SPF value. The clear formulas, which were found to be sprayable, were made by mixing the ingredients of sub-formulation I, then adding sub-formulation II and mixing, and then mixing in the ingredients of sub-formulation III. The SPF values were measured on a Labsphere UV 1000S Ultraviolet Transmittance Analyzer.

The SPF for the formula without the VA/butyl maleate/isobornyl acrylate copolymer (65-1) was 59, and the copolymer was found to boost SPF to 93 for the other formula (65-2).

Table 13: The clear, sprayable sunscreens of Example 11

| ingredient | trade name | addition level (parts by weight) | |
|---|---|---|---|
| | | 65-1 | 65-2 |
| sub-formulation I | | | |
| ethanol | | 40.0 | 42.0 |
| VA/butyl maleate/isobornyl acrylate copolymer | Advantage ® Plus | | 2.0 |
| sub-formulation II | | | |
| avobenzone | Escalol ® 517 | 3.0 | 3.0 |
| oxybenzone | Escalol ® 567 | 6.0 | 6.0 |
| homosalate | Eusolex ® HMS | 15.0 | 15.0 |
| octisalate | Escalol ® 587 | 5.0 | 5.0 |
| octocrylene | Escalol ® 597 | 10.0 | 10.0 |
| sub-formulation III | | | |
| diisopropyl adipate | Ceraphyl ® 230 | 5.5 | 5.5 |
| isocetyl alcohol | Ceraphyl ® ICA | 2.5 | 2.5 |
| tridecyl neopentanoate | Ceraphyl ® 55 | 6.5 | 6.5 |
| lauryl lactate | Ceraphyl ® 31 | 4.5 | 4.5 |
| total | | 100.0 | 100.0 |

Example 12

Three ethanol-based sunscreens were made having the acrylates/C12-C22 alkyl methacrylate copolymer (Allianz™ OPT) and either isohexadecane, cyclomethicone, or disopropyl adipate/diethylhexyl malate (Table 14). First, Allianz™ OPT was added and mixed into a pre-made SPF-70 base. Then, the ethanol was added with mixing, followed by the remaining ingredient(s).

All three sunscreen were hazy. Formula 85-1 with isohexadecane showed a clarity advantage over formulas 85-2 and 85-3.

Table 14: The sunscreen formulas of Example 12

| ingredient | | addition level (parts by weight) | | |
|---|---|---|---|---|
| pre-made base | trade name | 85-1 | 85-2 | 85-3 |
| avobenzone | Escalol ® 517 | 3.0 | 3.0 | 3.0 |
| oxybenzone | Escalol ® 567 | 6.0 | 6.0 | 6.0 |
| homosalate | Eusolex ® HMS | 15.0 | 15.0 | 15.0 |
| octisalate | Escalol ® 587 | 5.0 | 5.0 | 5.0 |
| octocrylene | Escalol ® 597 | 10.0 | 10.0 | 10.0 |
| acrylates/C12-C22 alkylmethacrylate copolymer | Allianz ™ OPT | 1.0 | 1.0 | 1.0 |
| ethanol | | 51.0 | 51.0 | 51.0 |
| isohexadecane | Permethyl ® 101A | 9.0 | | |
| cyclomethicone | | | 9.0 | |
| diisopropyl adipate | Ceraphyl ® 230 | | | 4.5 |
| diethylhexyl malate | Ceraphyl ® 45 | | | 4.5 |
| total | | 100.0 | 100.0 | 100.0 |

Example 13

A pre-made clear, sprayable sunscreen formulation of the invention was reformulated to contain 1% of the acrylates/C12-C22 alkyl methacrylate copolymer (Allianz™ OPT) (Table 15). This pre-made formula contained 40% (w/w) ethanol.

The post-formulation sunscreen showed a slight haze, but was found to be clear when sprayed on wet skin. The formula was placed overnight in a freezer at −20° C., and was found to be stable without separation or sedimentation the next day. The SPF value for 86-1 was measured to be 67 using a Labsphere UV 2000S Ultraviolet Transmittance Analyzer.

TABLE 15

The sunscreen formula of Example 13

| ingredient pre-made formula | trade name | addition level (parts by weight) 86-1 |
|---|---|---|
| -65-1 (from Example 11) | | 99.0 |
| acrylates/C12-C22 alkyl methacrylate copolymer | Allianz ™ OPT | 1.0 |
| total | | 100.0 |

Example 14

Formula 65-1 of Example 11 was modified by removing the VA/butyl maleate/isobornyl acrylate copolymer and incorporating 1% of the acrylates/C12-C22 alkyl methacrylate copolymer (Allianz™ OPT) (Table 16).

The product exhibited a slight haze, but sprayed clear on wet skin. It appeared more water resistant than formula 65-1. After spraying on wet skin and drying, formula 87 imparted an elegant feel to the skin and left less shine than the formula without the acrylates/C12-C22 alkyl methacrylate copolymer. The SPF was found to be 102, as measured by a Labsphere UV 2000S Ultraviolet Transmittance Analyzer, and the product was stable after leaving overnight in a freezer at −20° C.

TABLE 16

The clear sprayable sunscreen formula of Example 14

| ingredient | trade name | addition level (parts by weight) 87 |
|---|---|---|
| sub-formulation I | | |
| ethanol | | 41.0 |
| acrylates/C 12-C22 alkyl methacrylate copolymer | Allianz ™ OPT | 1.0 |
| sub-formulation II | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 10.0 |
| sub-formulation III | | |
| diisopropyl adipate | Ceraphyl ® 230 | 5.5 |
| isocetyl alcohol | Ceraphyl ® ICA | 2.5 |
| tridecyl neopentanoate | Ceraphyl ® 55 | 6.5 |
| lauryl lactate | Ceraphyl ® 31 | 4.5 |
| total | | 100.0 |

Example 15

Two sprayable SPF-70 sunscreen formulas were made with the acrylates/C12-C22 alkyl methacrylate copolymer (Allianz™ OPT) and ethanol (Table 17). The first formula contained 50% (w/w) ethanol, and the second contained 60% (w/w) ethanol. They were prepared by first heating sub-formulation I (pre-made) to 45° C., and then blending in sub-formulation II. The heat was turned off, and then the acrylates/C12-C22 alkyl methacrylate copolymer was added. Ethanol was mixed in last until the entire sunscreen was uniform.

Formula 102-1, which contained 50% ethanol, was hazy after being made, but sprayed clear on wet skin. Formula 102-2, which contained 60% ethanol, was almost opaque after preparation, and turned white when sprayed onto wet skin. Both formulations showed a precipitate after 5 freeze at −20° C./thaw cycles.

TABLE 17

The sprayable SPF-70 sunscreen formulas of Example 15

| ingredient | trade name | addition level (parts by weight) | |
|---|---|---|---|
| | | 102-1 | 102-2 |
| sub-formulation I | | | |
| avobenzone | Escalol ® 517 | 3.00 | 3.00 |
| oxybenzone | Escalol ® 567 | 6.00 | 6.00 |
| homosalate | Eusolex ® HMS | 15.00 | 15.00 |

TABLE 17-continued

The sprayable SPF-70 sunscreen formulas of Example 15

| ingredient | trade name | addition level (parts by weight) 102-1 | 102-2 |
|---|---|---|---|
| octisalate | Escalol ® 587 | 5.00 | 5.00 |
| octocrylene | Escalol ® 597 | 10.00 | 10.00 |
| sub-formulation II | | | |
| diisopropyl adipate | Ceraphyl ® 230 | 2.60 | 0.00 |
| isocetyl alcohol | Ceraphyl ® ICA | 1.45 | 0.00 |
| tridecyl neopentanoate | Ceraphyl ® 55 | 3.80 | 0.00 |
| lauryl lactate | Ceraphyl ® 31 | 2.15 | 0.00 |
| sub-formulation III | | | |
| ethanol | | 50.00 | 60.00 |
| acrylates/C12-C22 alkyl methacrylate copolymer | Allianz ™ OPT | 1.00 | 1.00 |
| total | | 100.00 | 100.0 |

Example 16

A clear gel SPF-50 sunscreen formula was made containing lightly- to moderately-crosslinked PVP (Table 18). To make the sunscreen, first the crosslinked PVP of sub-formulation I was added to the ethanol with homogenization. Sub-formulation II (which was pre-made) was added to sub-formulation I. Then, ingredients of sub-formulation III were added with mixing. The resulting product was clear and golden yellow in color.

The clear gel sunscreen was found to have a Brookfield viscosity of 9,600 cP (spindle T-B at 10 rpm, room temperature). The sunscreen formed a silky-smooth layer on dry skin. Furthermore, the sunscreen remained clear and did not turn white when applied to wet skin.

TABLE 18

The clear gel SPF-50 sunscreen formulas of Example 16

| ingredient | trade name | addition level (parts by weight) 184-134 |
|---|---|---|
| sub-formulation I | | |
| ethanol | | 38.0 |
| lightly- to moderately-crosslinked PVP | FlexiThix ™ | 4.0 |
| sub-formulation II | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 8.0 |
| sub-formulation III | | |
| isocetyl alcohol | Ceraphyl ® ICA | 3.0 |
| tridecyl neopentanoate | Ceraphyl ® 55 | 7.0 |
| lauryl lactate | Ceraphyl ® 31 | 5.0 |
| total | | 100.0 |

Example 17

A gel SPF-50 sunscreen formula was made containing lightly- to moderately-crosslinked PVP and the acrylates/C12-C22 alkyl methacrylates copolymer (Table 19). First, sub-formulation I was mixed with gentle heating to 45° C. Then, the ingredients of sub-formulation II were blended in and the heat turned off. The acrylates/C12-C22 alkyl methacrylates copolymer was added and mixed well until smooth. At this point, ethanol was added, followed by the PVP and homogenized until a uniform sunscreen was produced. The final product was observed to have an almost imperceptible haze.

The Brookfield viscosity of the sunscreen was 11,700 cP (spindle T-B at 10 rpm, room temperature). When applied to wet skin, the clear gel sunscreen did not turn white.

Increasing the amount of lauryl lactate to 6% (with a corresponding 1% reduction in ethanol) reduces the haze. The corresponding viscosity for this reformulated sunscreen was 13,800 cP (spindle T-B at 10 rpm, room temperature).

TABLE 19

The clear, gel SPF-50 sunscreen formulas of Example 17

| ingredient | trade name | addition level (parts by weight) 184-136 |
|---|---|---|
| sub-formulation I | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 8.0 |
| sub-formulation II | | |
| diisopropyl adipate | Ceraphyl ® 230 | 6.0 |
| isocetyl alcohol | Ceraphyl ® ICA | 3.0 |
| tridecyl neopentanoate | Ceraphyl ® 55 | 7.0 |
| lauryl lactate | Ceraphyl ® 31 | 5.0 |
| acrylates/C12-C22 alkyl methacrylate copolymer | Allianz ™ OPT | 1.0 |
| ethanol | | 37.0 |
| lightly- to moderately-crosslinked PVP | FlexiThix ™ | 4.0 |
| total | | 100.0 |

Example 18

A clear gel SPF-50 sunscreen formula was made containing lightly- to moderately-crosslinked PVP and the acrylates/C12-C22 alkyl methacrylates copolymer (Table 20). The procedure for making it was identical to Example 17. The final product was observed to have an almost imperceptible haze.

The sunscreen was clear and did not whiten when applied to wet skin.

Additionally, a clear, gel sunscreen also was made having 2% trimethylsiloxyphenyl dimethicone (Si-Tec™ PTM 20, ASI) post-added on top of this Example's formula.

TABLE 20

The clear, gel SPF-50 sunscreen formulas of Example 18.

| ingredient | trade name | addition level (parts by weight) 184-143 |
|---|---|---|
| sub-formulation I | | |
| avobenzone | Escalol ® 517 | 3.0 |
| oxybenzone | Escalol ® 567 | 6.0 |
| homosalate | Eusolex ® HMS | 15.0 |

TABLE 20-continued

The clear, gel SPF-50 sunscreen formulas of Example 18.

| ingredient | trade name | addition level (parts by weight) 184-143 |
|---|---|---|
| octisalate | Escalol ® 587 | 5.0 |
| octocrylene | Escalol ® 597 | 8.0 |
| sub-formulation II | | |
| diisopropyl adipate | Ceraphyl ® 230 | 6.0 |
| isocetyl alcohol | Ceraphyl ® ICA | 3.0 |
| tridecyl neopentanoate | Ceraphyl ® 55 | 6.0 |
| lauryl lactate | Ceraphyl ® 31 | 8.0 |
| ethanol | | 35.0 |
| acrylates/C12-C22 alkyl methacrylate copolymer | Allianz ™ OPT | 1.0 |
| lightly- to moderately-crosslinked PVP | FlexiThix ™ | 4.0 |
| total | | 100.0 |

Example 19

A gel SPF-50 sunscreen formula was made containing lightly- to moderately-crosslinked PVP, acrylates/C12-C22 alkyl methacrylates copolymer, and hydroxypropylcellulose (Table 21). First, the ingredients listed under sub-formulation I were mixed with gentle heating to 45° C. Then, the ingredients of sub-formulation II were added with mixing. After turning off the heat, the hydroxypropylcellulose was added, dispersed and blended until smooth and clear. Then, the acrylates/C12-C22 alkyl methacrylates copolymer was blended in followed by separate additions of ethanol and the lightly- to moderately-crosslinked PVP.

The sunscreen had a measured Brookfield viscosity of 22,000 cP (spindle T-B, 10 rpm, room temperature), and took the appearance of a hazy gel. When applied to wet skin, the sunscreen did not turn white. Furthermore, the sunscreen did not pill after skin application.

TABLE 21

The gel SPF-50 sunscreen formulas of Example 19

| ingredient | trade name | addition level (parts by weight) 270-90 |
|---|---|---|
| sub-formulation I | | |
| avobenzone | Escalol ® 517 | 3.0 |
| oxybenzone | Escalol ® 567 | 6.0 |
| homosalate | Eusolex ® HMS | 15.0 |
| octisalate | Escalol ® 587 | 5.0 |
| octocrylene | Escalol ® 597 | 8.0 |
| sub-formulation II | | |
| diisopropyl adipate | Ceraphyl ® 230 | 6.0 |
| isocetyl alcohol | Ceraphyl ® ICA | 3.0 |
| tridecyl neopentanoate | Ceraphyl ® 55 | 7.0 |
| lauryl lactate | Ceraphyl ® 31 | 5.0 |
| hydroxypropylcellulose | Klucel ™ H CS | 0.5 |
| acrylates/C12-C22 alkyl methacrylate copolymer | Allianz ™ OPT | 1.0 |
| ethanol | | 38.2 |
| lightly- to moderately-crosslinked PVP | FlexiThix ™ | 2.3 |
| total | | 100.0 |

What is claimed is:

1. A substantially anhydrous sun-care product comprising: (A) a cosmetically-acceptable, substantially non-aqueous vehicle comprising at least 10% by weight esters based on the total weight of the non-aqueous vehicle, and (B) a UV active, wherein the non-aqueous vehicle comprises an alcohol selected from the group consisting of ethanol, 1-propanol, 2-propanol, and combinations thereof; and an ester such that the dielectric constant of the non-aqueous vehicle is about 20 or less and the sun-care product is substantially non-whitening upon application to wet skin; wherein the sun-care product comprises no more than 10% (w/w) water and having 50% (w/w) or less of the alcohol.

2. The sun-care product according to claim 1 having from 30% (w/w) to 45% (w/w) of the alcohol.

3. The sun-care product according to claim 1 wherein said UV active is selected from the group consisting of: 4-methylbenzylidene camphor, avobenzone, bemotrizinol, benzophenone-1, benzophenone-2, benzophenone-3 (oxybenzone), benzophenone-4 (sulisobenzone), benzophenone-5 (sulisobenzone sodium), benzophenone-6, benzophenone-8 (dioxybenzone), benzophenone-9, benzylidene camphor sulfonic acid, bisdisulizole disodium, bisoctrizole, camphor benzalkonium methosulfate, cinoxate, DEA methoxycinnamate, diethylamine hydroxybenzoyl hexylbenzoate, digalloyl trioleate, diisopropyl methylcinnamate, dimethoxyphenyl-[1-(3,4)]-4,4-dimethyl 1,3-pentanedione, drometrizole, drometrizole trisiloxane, ecamsule, ensulizole, ethylhexyl p-methoxycinnamate, ethylhexyl triazone, ferulic acid, glyceryl ethylhexanoate dimethoxycinnamate, homomenthyl salicylate (homosalate), iscotrizinol, isoamyl-p-methoxycinnamate, lisadimate, meradimate, camphor benzalkonium methosulfate, octocrylene, octyl dimethyl PABA (padimate O), octyl salicylate (octisalate), p-aminobenzoic acid (PABA), PEG-25 PABA, pentyl dimethyl PABA (padimate A), polysilicone-15, roxadimate, titanium dioxide, trolamine salicylate, zinc oxide, and combinations thereof.

4. The sun-care product according to claim 3 wherein each said UV active is present in an amount from 0.5% (w/w) to 40% (w/w).

5. The sun-care product according to claim 1 having from 50% (w/w) to 99% (w/w) or more of said cosmetically-acceptable, non-aqueous vehicle.

6. The sun-care product according to claim 5 wherein said cosmetically-acceptable, non-aqueous vehicle comprises components selected from the group consisting of: esters, glycols, hydrocarbons, oils, and combinations thereof.

7. The sun-care product according to claim 6 wherein said cosmetically-acceptable, non-aqueous vehicle comprises components selected from the group consisting of: diisopropyl adipate, ethanol, hexylene glycol, isodecyl neopentanoate, isostearyl neopentanoate, phenethyl benzoate, polydimethylsiloxane, silicones, isocetyl alcohol, tridecyl neopentanoate, lauryl lactate, diisopropyl adipate, diethylhexyl malate, cyclomethicone, isohexadecane, and combinations thereof.

8. The sun-care product according to claim 1 having a sun protection factor (SPF) of at least 15.

9. The sun-care product according to claim 1 that is a mist, a spray, an aerosol, a mousse, a gel, a solution, or a dispersion.

10. The sun-care product according to claim 1 wherein said non-aqueous vehicle comprises from about 20%-50% by weight esters based on the total weight of the non-aqueous vehicle.

11. A substantially anhydrous sun-care product comprising: (A) a cosmetically-acceptable, substantially non-aqueous vehicle comprising at least 10% by weight esters based on the total weight of the non-aqueous vehicle, and (B) a UV active, wherein said non-aqueous vehicle comprises an alcohol selected from the group consisting of ethanol, 1-propanol, 2-propanol, and combinations thereof; in an amount of 50% (w/w) or less based on the weight of the sun-care product and an ester the sun-care product is substantially non-whitening upon application to wet skin; wherein the sun-care product comprises no more than 10% (w/w) and having 50% (w/w) or less of the alcohol.

12. The sun-care product according to claim 11 wherein said non-aqueous vehicle comprises from about 20%-50% by weight esters based on the total weight of the non-aqueous vehicle.

13. The sun-care product according to claim 12 wherein said esters are selected from the group consisting of diisopropyl adipate, isodecyl neopentanoate, isostearyl neopentanoate, phenethyl benzoate, tridecyl neopentanoate, lauryl lactate, diisopropyl adipate, diethylhexyl malate and combinations thereof.

14. A method of protecting keratinous substances from UV radiation, said method comprising applying said sun-care product of claim 1 on said keratinous substance.

15. The method according to claim 14 wherein said keratinous substance is the epidermis or hair of a mammal.

\* \* \* \* \*